United States Patent
Ručman et al.

Patent Number: 5,480,885
Date of Patent: Jan. 2, 1996

[54] ERGOLINE DERIVATIVES OF 1-PROPINYLAMINE, A PROCESS FOR THE MANUFACTURE THEREOF AND THE USE THEREOF FOR MEDICAMENTS

[75] Inventors: Rudolf Ručman; Breda Bole-Vunduk; Magdalena Ocvirk; Bogomila Lavrič; Igor Krisch, all of Ljubljana, Slovenia

[73] Assignee: Lek, Tovarna Farmacevtskih in Kemicnih, Verovskova, Slovenia

[21] Appl. No.: 160,271

[22] Filed: Dec. 2, 1993

Related U.S. Application Data

[63] Continuation-in-part of Ser. No. 901,983, Jun. 22, 1992, Pat. No. 5,288,724.

[30] Foreign Application Priority Data

Jul. 1, 1991 [YU] Yugoslavia ............... 1154/91

[51] Int. Cl.$^6$ ................... A61K 31/44
[52] U.S. Cl. ............... 514/288; 546/67; 546/69
[58] Field of Search ............ 546/67, 69; 514/288

[56] References Cited

U.S. PATENT DOCUMENTS

| | | | |
|---|---|---|---|
| 3,228,944 | 1/1966 | Bernardi | 546/69 |
| 3,346,580 | 10/1967 | Hofmann et al. | 546/69 |
| 4,064,249 | 12/1977 | Mago | 546/69 |

*Primary Examiner*—Richard D. Lovering
*Assistant Examiner*—Catherine S. Kilby Scalzo
*Attorney, Agent, or Firm*—Pollock, Vande Sande & Priddy

[57] ABSTRACT

A method of treating psychosis including administering an antipsychotically effective amount of an ergolinyl derivative of 2-propinylamine of the formula I

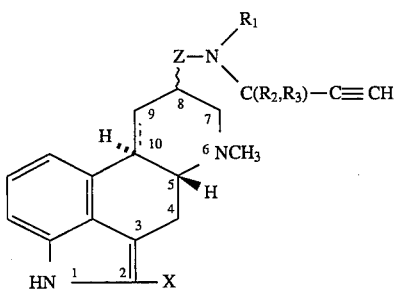

wherein, $R_1$, $R_2$, and $R_3$ independently represent a hydrogen atom or a straight-chain or branched-chain $C_1$–$C_6$ alkyl group, X represents a hydrogen or a halogen atom, Z represents a carbonyl or methylene group, and $C_9$═$C_{10}$ represents a single or a double, diastereomeric forms, racemates and acid addition salts thereof.

3 Claims, No Drawings

ERGOLINE DERIVATIVES OF 1-PROPINYLAMINE, A PROCESS FOR THE MANUFACTURE THEREOF AND THE USE THEREOF FOR MEDICAMENTS

CROSS REFERENCES TO RELATED APPLICATIONS

This is a continuation-in-part of U.S. application Ser. No. 07/901,983, filed Jun. 22, 1992, now U.S. Pat. No. 5,288,724 and entitled "Novel Ergoline Derivatives of 2-Propinylamine, A Process, for the Manufacture Thereof and the Use Therefor for Medicaments, disclosure of which is incorporated herein by reference.

TECHNICAL FIELD OF THE INVENTION

The present invention belongs to the field of pharmaceutical industry and refers to novel ergoline derivatives of optionally substituted 2-propinylamine, which are useful in the pharmaceutical industry as active substances for the manufacture of medicaments used in the treatment of hypertension, migraine, anxiety states, depressions, obesity, psychotic disorders, including schizophrenia.

1. Technical Problem

A constant need exists for novel, biologically highly active ergoline derivatives, which are suitable for use in human medicine.

2. Prior Art

Numerous ergoline compounds and processes for the manufacture thereof are known from published articles and patent literature, e.g. A Stoll and A. Hoffmann, Helv. Chim. Acta 26, 922 (1943), W. L. Garbrecht, J. Org. Chem. 24, 368 (1959), and CH 469 735, CS 105 954, U.S. Pat. Nos. 3,141,887, and 2,736,728, respectively.

DESCRIPTION OF THE SOLUTION TO THE TECHNICAL PROBLEM

The present invention relates to novel ergoline derivatives of optionally substituted 2-propinylamine of the general formula I

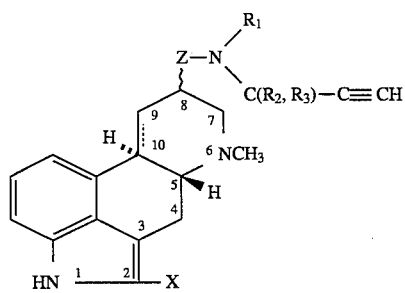

Wherein, $R_1$, $R_2$ and $R_3$ independently represent a hydrogen atom or a straight-chain or branched-chain $C_1$–$C_6$ alkyl group, X represents a hydrogen or a halogen atom, Z represents a carbonyl or methylene group and $C_9 \ldots C_{10}$ represents a single or a double bond, 20 and to the acid addition salts thereof.

Since the compounds of the general formula I contain a chiral center on the 8-position, they can exist in the form of diastereoisomers having 8α- or 8β- configuration or in the form of a mixture of both diastereoisomers. The invention encompasses both pure diastereoisomers as well as mixtures thereof and racemates.

The pharmaceutically acceptable acid addition salts of the compound of the general formula I are prepared with physiologically acceptable organic or inorganic acids such as acetic, formic, maleic, tartaric, citric, methanesulfonic, hydrobromic, hydrochlorid, sulphuric acids etc.

Novel ergoline derivatives of 2-propinylamine of the general formula I can be prepared in accordance with known methods described in the literature; however, the process of the present invention is preferable and gives the best results.

According to the invention, the compounds of the general formula I are prepared by condensing a compound of formula II

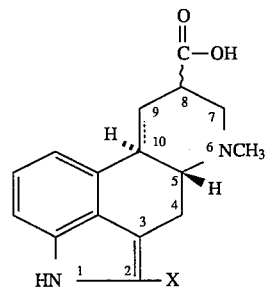

wherein the bond between the $C_9$ and $C_{10}$ is a single or a double one, with an N-substituted 2-propinylamine of the general formula III

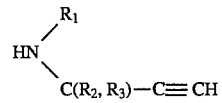

wherein the Substituents are as defined hereinbefore, to a compound of the general formula IV

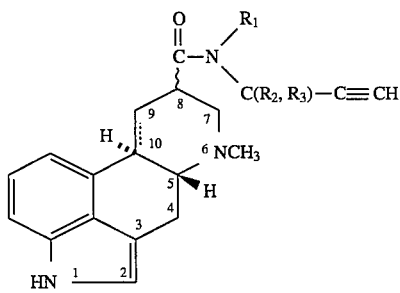

wherein $R_1$, $R_2$, $R_3$ and $C_9 \ldots C_{10}$ are as defined hereinbefore, which is isolated, purified and selectively halogenated at the 2-position.

Optionally, a compound of the general formula I, wherein Z represents a carbonyl group and wherein $R_1$, $R_2$, $R_3$ and $C_9 \ldots C_{10}$ are as defined hereinbefore, can be reduced to a corresponding compound of the general formula I, wherein Z represents a methylene group, which compound is selectively brominated at the 2-position.

The condensation of the compound of the formula II with a compound of the general formula III is carried out in an inert organic solvent such as dimethylformamide, in the presence of a condensing agent such as diphenylphosphorylazide (DPPA), and of an organic base such as triethylamine.

The selective halogenation of a compound of the general formula IV is carried out by means of mild halogenating agents such as N-bromosuccinimide, pyrrolidone-(2)hydrotribromide, N-chloro-2,6-dichloro-4-nitroacetanilide or 3-bromo-6-chloro-2-methylimidazo(1,2-b)piridazine dibromide, in an inert organic solvent such as dioxane or methylene chloride or in a mixture of organic solvents. Methods can be used that were described by R. Rucman, J. Korsic and M. Jurgec, Il Farmaco, Ed. Sci. 38,406 (1983) and in CH 263 279.

The reduction of a compound of the general formula I, wherein Z represents a carbonyl group, to a compound of the general formula I, wherein Z represents a methylene group, is carried out by means of well-known reducing agents such as sodium aluminium bis-(2-methoxyethoxy)dihydride, in an inert organic solvent such as toluene, at temperatures between room temperature and 100° C., preferably at about 60° C.

The inventive compounds of the general formula I are biologically highly active. Their effects were demonstrated in pharmacological tests and binding studies in different receptor models as shown hereinafter.

The compounds of the general formula I can be used medicaments in the form of pharmaceutical compositions containing these compounds, optionally together with acceptable pharmaceutical carriers. The compounds can be used as medicaments e.g. in the form of pharmaceutical compositions containing these compounds in mixtures with organic or inorganic pharmaceutical carriers suitable for enteral or parenteral application such as .water, gum arabic, gelatine, lactose, starch, magnesium stearate, talc, vegetable oils, polyglycols, etc., and various other auxiliary substances. The dosage unit of the composition contains from 0.001 to 10 mg of the compound of the invention.

The daily dose is from 0.0001 to 0.1 mg of the active substance per kg of body weight.

Another aspect of the invention is the use of the inventive compounds in the manufacture of medicaments that can be used in the treatment and prevention of diseases, such as hypertension, migraine, anxiety states, depressions, obesity, and psychotic disorders.

A further object of the invention are medicaments containing one of the compounds of the invention of the general formula I and/or physiologically acceptable acid addition salts thereof.

The novel ergoline derivatives of the present invention possess an extraordinarily potent antipsychotic and potentially anxiolytic and antidepressant action.

It has been found pursuant to the present invention that the strongest antipsychotic action is shown by the compound of Example 5, and particularly by the compound of Example 8 having the following structural formula:

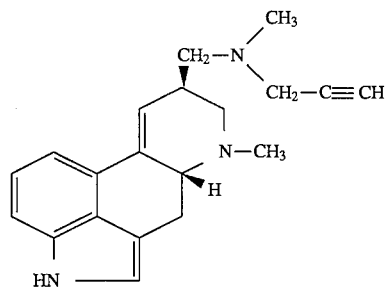

which expresses a lesser degree of probability of the development of extrapyramidal, central depressant and hypotensive side effects. The novel ergoline derivatives of the present invention are classified in class 4 of J. Gerlach's classification, i.e., into the group having the most distinct antipsychotic effects (antiphsychotics blocking $D_2$+other receptors).

The novel ergoline derivatives of the present invention excel by their mechanism of action (an agonistic or antagonistic action on the level of $5-HT_{1A}$ receptors and at the same time, an antagonistic action on the level of $D_2+5\ HT_2$ receptors). Such novel ergoline derivatives are advantageous in alleviating the syptoms of psychotic disorders as they are effective both as $5-HT_{1A}$ agonists and as $5-HT_2$ and $D_2$ antagonists.

The binding studies show that both compounds 5 and 8 exhibit a high affinity for the dopaminergic ($D_2$) and serotoninergic ($5-HT_2$) receptors, which the affinities for the dopaminergic ($D_1$) and adrenergic ($\alpha_1$) receptors are lower (table 2 hereinafter).

The novel ergoline derivatives of the present invention exhibit strong antagonistic action on $D_2$ abd $5-HT_2$ receptors and weak action on the level of $\alpha_1$ receptors and produce relatively small side effects in the sense of neurological effects on the extrapyramidal system (muscle rigidity, tremor and other parkinsonism-like effectes, akathisia, dyskinesia), hypotensions and central depressant effects. The vasoconstrictory action of the tested compounds is negligible, so that ergotism is not likely to develop.

The present invention is illustrated by the following examples:

EXAMPLE 1

9,10-Didehydro-N-(2'-propinyl)-6-methylergoline-8β-carboxamide D-lysergic acid (30 g, 0.112 moles) was suspended in dry dimethylformamide (DMF) (600 ml). 2-Propinylamine (15 ml, 0.2187 moles) and diphenylphosphorylazide (DPPA) (36 ml, 0.1668 moles) were added thereto, the mixture was stirred at room temperature for 10 minutes, which was followed by a slow addition of dry triethylamine (24 ml, 0.172 moles) and stirring for another 2 hours at room temperature.

The reaction mixture was then evaporated in vacuo to a thick gum, which was dissolved in methylene chloride (600 ml). The resulting solution was shaken with a 2% ammonia solution (2×600 ml). The organic phase was separated, dried over sodium sulfate and the solvent was evaporated in vacuo. The obtained dry title compound (49.3 g) was purified by chromatography over a column (7×36 cm) packed with basic aluminium oxyde (1800 g; Merck Geduran 90, activity II.–III.).

Fractions 20 to 30 yielded 14.53 g of the compound, which did not crystalize as the free base but did as the tartrate from ethanol. Thus, there were obtained 14.6 g (28.8%) of the title compound in the form of tartrate, m.p. 148°–150° C. Specific rotation [α]=–66.4° (c=1, $CHCl_3$)

EXAMPLE 2

2-Bromo-9,10-didehydro-N-(2'-propinyl)-6-methylergoline-8β-carboxamide

The compound obtained in Example 1 (4.9 g, 0.016 moles) was dissolved in a mixture of methylene chloride and dioxan (85:15; 400 ml). Finely ground pyrrolidone-(2)hydrobromide (5g, corresponding to 0.024 moles of $Br_2$) was added all at once under stirring and the mixture was stirred for 40 minutes. The reaction was stopped by the addition of ammonia, the mixture was filtered and the filtrate was washed with sodium bicarbonate (2×600 ml of a 2% solution). The methylene chloride solution was evaporated to dryness and the crude substance (3.82 g) was purified by chromatography over a column (4×15 cm) packed with silica gel (Merck 60, 0.063–0.200 mm, 92 g). Elution was carried out with a mixture of methylene chloride and acetone (80:20). Fractions 17 to 26 (of 50 ml each) were evaporated and the dry residue (1.01 g) was crystallized as oxalate from methanol/ether. The title compound was obtained in the form of oxalate (1.18 g), m.p. 169°–173° C. Yield: 15.5% of the theory. Specific rotation [α]=−78.2° (c=0.5, CHCl₃)

EXAMPLE 3

9,10-Didehydro-N-methyl-N-(1',1'-diethyl-2'-propinyl)-6-methylylergoline-8α-carboxamide According to the procedure as described in Example 1, D-lysergic acid was reacted with N-methyl-N-(1',1'-diethyl-2'-propinyl)amine. The yield of the title compound was 24.4% of the theory, m.p. 143°–148° C. Specific rotation [α]=+342° (c=0.5, CH₃OH)

EXAMPLE 4

9,10-Didehydro-N-methyl-N-(2'-propinyl)-6-methylergoline-8β-carboxamide

According to the procedure as described in Example 1, D-lysergic acid was reacted with N-methyl-N-(2'-propinyl)amine. The title compound was crystallized as tartrate from methanol. Yield: 34.6% of the theory, m.p. 140°–144° C. Specific rotation [α]=+30.1° (c=1, CH₃OH)

EXAMPLE 5

2-Bromo-9,10-didehydro-N-methyl-N-(2'-propinyl)-6-methylergo-line-8β-carboxamide According to the procedure as described in Example 2, 9,10-didehydro-N-methyl-N-(2'-propinyl)-6-methylergoline-8μ-carboxamide was brominated. The title compound was crystallized from ethanol. Yield: 42.9% of the theory, m.p. 119°–123° C. Specific rotation [α]=+30.1° (c=1, CH₃OH)

EXAMPLE 6

N-Methyl-N-(2'-propinyl)-6-methylergoline-8β-carboxamide 9,10-Dihydrolysergic acid (8.0 g, 0.0296 moles, dried in vacuo at 120° C.) and N-methyl-N-(2'-propinyl)amine (4.01 g, 0.058 moles) were suspended in DMF (200 ml, dried with 3×10⁻⁴ μm molecular sieves). DPPA (4 ml, 0.0436 moles) was added thereto under stirring, which was continued for another 15 minutes, and triethylamine (6.4 g, 0.046 moles, dried over NaOH and then distilled) was added thereto. The reaction mixture was stirred at room temperature for 6 hours. The unreacted 9,10-dihydrolysergic acid (1.33 g=16.6%) was filtered off as a white solid. The filtrate was evaporated in vacuo to a thick gum, which was dissolved in a mixture of ethyl acetate and methylene chloride (1:1, 300 ml) and washed with a 2% ammonia solution (3×300 ml). The organic phase was dried over Na2SO₄, purified with activated charcoal and concentrated in vacuo to a small volume. The white solid, which crystallized, was filtered off and recrystallized from dimethyl sulphoxide by addition of water. The yield of the title compound was 7.54 g (79.25~o of the theory), m.p. 194°–196° C. Specific rotation [α]=+71.0° (c=0.5, CHCl₃)

EXAMPLE 7

2-Bromo-N-methyl-N-(2'-propinyl)-6-methylergoline-8β-carboxamide 9,10-Dihydrolysergic acid N-methyl-N-(2'-propinyl)amide (0.64 g, 2 mmoles) was dissolved in a nitrogen atmosphere in a mixture of methylene chloride and dioxan (80:20, 20 ml), and pyrrolidone-(2)-hydrotribromide (1.22 g, 3 mmoles) in CHCl₂ (220 ml) was added thereto. The reaction mixture was stirred for 20 minutes. The solution was then washed with a 2% aqueous ammonia solution (3×300 ml). The organic phase was dried over Na₂SO₄ and the solvent was evaporated in vacuo. The obtained brown residue (1.21 g) was purified by chromatography over a column (2×30 cm) packed with silica gel (Merck 60, 0.040 to 0.063 mm, 60 g). The elution was carried out with a mixture of methylene chloride and acetone (8:2). Fractions containing the title compound were evaporated in vacuo. The obtained residue (0.85 g) was crystallized from boiling ethyl acetate. The obtained white title compound (0.67 g, 83.7% of the theory) had a m.p. of 239°–243° C. Specific rotation [α]=−100.8° (c=1, CH₂Cl₂/CH₃OH=1:1)

EXAMPLE 8

8β-Methyl-N-methyl-N-(2'-propinyl)-6-methylergoline

D-Lysergic acid N-methyl-N-(2'-propinyl) amide (7.51 g, 0.0235 moles) was dissolved in anhydrous toluene (900 ml) at 60° C. To the solution, sodium aluminium bis(2-methoxyethoxy)-dihydride (38.38 g, a 70% solution in benzene) was gradually added under stirring at 60-70° C. and the stirring was continued for another hour. The mixture was cooled, ethanol (96~o, 20 ml) and a 2% aqueous solution of sodium hydroxyde (200 ml) were added, and the layers were separated. The organic phase was extracted with a 2% aqueous solution of sodium hydroxyde (2×500 ml ), dried over Na₂2SO₄ and evaporated to dryness in vacuo. The residue was dissolved in methylene chloride and the solvent was partly evaporated; the crude product that crystallized was recrystallized from a mixture of ethyl acetate and methylene chloride (1:1) while the solvent was slowly evaporated in vacuo. The title compound (4.04 g, 56.28% of the theory) had a m.p. of 203°–205° C. (with decomposition). Specific rotation [α]=+59.5° (c=1, CHCl₃)

EXAMPLE 9

2-Bromo-8β-methyl-N-methyl-N-(2'-propinyl)-6-methylergoline

N-methyl-N-(2'-propinyl)-lysergamine (1.65 g, 5.4 mmoles) was dissolved in a mixture of methylene chloride and dioxan (85:15, 20 ml). Pyrrolidone-(2)-hydrotribromide (6.6 g, corresponding to 12 mmoles of Br2) was added thereto under stirring at 10° C. and the stirring was continued for 1 hour. The reaction mixture was filtered, the insoluble was washed with the above mixture of methylene chloride and dioxan (85:15, 100 ml) and the combined filtrates were washed with a saturated solution of sodium bicarbonate (2×100 ml). The organic phase was dried over Na2SO4 and evaporated to dryness. The obtained dry residue (1.70 g) was dissolved in a mixture of methylene chloride and ethyl acetate (1:1) and purified by chromatography over a column (3×20 cm) packed with silica gel (Merck 60, 0.2 to 0.063 mm, 64.6 g). The title compound was eluted with pure ethyl acetate. The appropriate fractions were evaporated to dryness in vacuo and dissolved in a mixture of ethyl acetate and methylene chloride (1:1). Following a partial evaporation of the solvent and standing overnight at −15° C. the title compound (0.67 g, 32.28% of the theory) was crystallized in the form of white crystals, m.p. 208°–212° C. Specific rotation $[\alpha]=+22.8°$ (c=0.5, $CH_3OH$)

Pharmacological Tests 9,10-Didehydro-N-(2-propinyl)-6-methylergoline-8β-carboxamide (compound of Example 1)

The compound caused a constriction of the isolated rabbit thoracic aorta The intrinsic activity was comparable to that of serotonin. At a concentration of 1 μM the vasoconstriction was the result of the activation of $\alpha_1$-adrenergic receptors.

On the isolated rat uterus (the method was described by De Jalon et al., Pharmacoter. act. 3, 313 (1945), hereinafter "Jalon"), it inhibited serotonin (2.47×10−8M)induced contractions ($IC_{50}=5.37\times10^{-1}M$).

The compound had no uterotonic activity (isolated rat uterus, see Jalon).

Approximately 2 minutes after an intravenous application of the compound (450 μg/kg) to pentobarbital-anesthetized normotensive rats, a strong reduction in the carotid artery pressure and heart rate set in, followed by exitus.

The intravenous application of the compound in a dose of 450 μg/kg to pithed rats in accordance with the method described by Gillespie et al., Br. J. Pharmacol. 40, 257–267 (1970) (hereinafter "Gillespie") caused a transient, yet very strong peripheral vasoconstriction.

In a dose of 4 mg/kg i.p. the compound inhibited the head twitch response after the injection of D,L-5-hydroxytryptophan/carbidopa (DL-5-HTP/carbidopa) by 62%. The substance was injected 15 minutes prior to DL-5-HTP. The head twitch was recorded from 30 to 35 minutes after the DL-5-HTP injection (modified method according to Handley and Singh, Br. J. Pharmacol. 86, 297 (1985)).

After an i.p. application of the substance in a dose of 5 mg/kg to mice, a very strong dilatation of the pupil occurred (the method was described by Pulewka in Archiv f. Experiment. Path. u. Pharmakol. 168, 37 (1932), hereinafter "Pulewka"). The mice became agitated, piloerection, tremor and excitation took place. After 60 minutes the effect was quickly reduced.

The binding studies showed that the compound possessed affinity to

[$^3$H] 8-OH-DPAT binding site ($S-HT_{1A}$ serotoninergic receptor); a further functional test indicated an agonistic activity;

[$^3$H] DTG binding site (sigma receptor); a further functional test indicated an antagonistic activity.

Note:
8-OH-DPAT=8-hydroxy-2-(di-n-propylamino)tetraline
DTG=1,3-di-o-toluylguanidine 2-Bromo-9,10-didehydro-N-(2'-propinyl)-6-methylergoline-8β-carboxamide (compound of Example 2)

On the isolated rabbit thoracic aorta the compound competitively inhibited the constrictive effect of serotonin ($pA_2=8.13$).

On the isolated rat uterus (see Jalon) it inhibited the serotonin-induced contractions ($IC_{50}=2.69\times10^{-8}M$).

At a concentration of 1000 ng/ml it caused a 100% blocking of spontaneous uterus contractions in rats (see Jalon).

The maximum reduction in carotid artery pressure (by 15%) and in heart rate (by 5%) with respect to initial levels set in immediately after the application of the compound (450 μg/kg, i.v.) to pentobarbital-anesthetized normotensive rats. The effect was of a transient nature (up to 20 minutes).

The i.p. application of the compound in a dose of 450 μg/kg to pithed rats (see Gillespie) caused a sustained mean increase of the diastolic pressure by 20% with respect to the control.

The i.p. application of the compound in a dose of 5 mg/kg to mice caused a marked dilatation of the pupil (see Pulewka).

The binding studies showed that the compound possessed affinity to

[$^3$H] 8-OH-DPAT binding site (5-$HT_{1A}$ serotoninergic receptor); a further functional test did not indicate any activity;

[$^3$H] DTG binding site (sigma receptor); a further functional test indicated an antagonistic activity.

9,10-Didehydro-N-methyl-N-(2'-propinyl)-6-methylergoline-8β-carboxamide (compound of Example 4)

The compound caused a constriction of the isolated rabbit thoracic aorta ($pD_2=6.41$). The intrinsic activity was comparable to that of serotonin. At a concentration of 0.39 μM ($EC_{50}$) it caused vasoconstriction, which was predominantly the result of the activation of $\alpha_1$-adrenergic receptors and to a lesser extent of the activation of 5-$HT_2$ receptors. At a preparation with inactivated $\alpha_1$-adrenergic receptors, the compound (0.01 to 0.3 μM) showed a serotonin-antagonistic activity. At smaller doses (0.1 μM) the antagonism was of competitive nature ($pA_2=8.37$), whereas at higher doses there was a noticeable decrease of the maximum activity of serotonin.

At a concentration of $3.20\times10^{-8}M$, it showed a uterotonic activity (see Jalon), which was lesser than the one of methylergometrine maleate ($5.49\times10^{-9}$ to $10.98\times10^{-9}M$).

When applied to pentobarbital-anesthetized normotensive rats (450 μg/kg, i.v.), the compound caused statistically non-significant changes in carotid artery pressure and a mean 20% decrease in the heart rate with respect to the initial level (respiratory troubles could be perceived).

An i.v. application of the compound (450 μg/kg) to pithed rats (see Gillespie) caused a transient, yet extraordinarily strong peripheric vasoconstriction.

The compound (0.125 to 4 mg/kg, i.p.) caused a head twitch response in mice. The maximum activity took place at a dose of 1 mg/kg i.p., at higher doses the activity decreased (autoinhibitory effect).

The compound caused a dose-dependent dilatation of the pupil in mice (see Pulewka), an increased activity, tremor and piloerection.

The acute toxicity in mice after intravenous application was $LD_{50}=55$ (47–63) mg/kg, determined in accordance with the method described by Miller and Tainter, Proc. Soc. Exptl. Biol. Med. 57, 261 (1944).

2-Bromo-9,10-didehydro-N-methyl-N-(2'-propinyl)-6-methylergoline-8β-carboxamide (compound of Example 5)

On the isolated rabbit thoracic aorta the compound competitively inhibited the constrictive activity of serotonin ($pA_2$=7.93) and noradrenaline ($pA_2$=6.45).

On the isolated rat uterus (see Jalon) it inhibited serotonin ($2.47 \times 10^{-8}$M)-induced contractions ($IC_{50}$=$1.25 \times 10^{-8}$M). It had no uterotonic activity (see Jalon).

An intravenous application of the compound in a dose of 450 µg/kg to pentobarbital-anesthetized normotensive rats caused a small, yet statistically significant decrease in carotid artery pressure and heart rate. The maximum effect set in immediately after the application of the compound (a 10% decrease with respect to the initial level), decreasing gradually with time.

An intravenous application of the compound (450 µg/kg) to pithed rats (see Gillespie) caused a slowly developing peripheric vasoconstriction (a 20% increase with respect to the control).

The compound ($ID_{50}$ =3.8 mg/kg, i.p.) inhibited the head twitch response in mice after the injection of L-5-HTP/carbidopa. The compound was injected 15 minutes prior to L-5-HTP (modified method according to Handley and Singh, Br. J. Pharmacol. 86, 297 (1985)).

The binding studies showed that the compound possessed affinity to

[$^3$H] 8-OH-DPAT binding site (5-HT$_{1A}$ serotoninergic receptor); a further functional test did not indicate any activity;

[$^3$H] DTG binding site (sigma receptor); a further functional test indicated an antagonistic activity.

8β-Methyl,N-methyl-Nr(2'-propinyl)-6-methylergoline (compound of Example 8)

On the isolated rabbit thoracic aorta the compound competitively inhibited the constrictive activity of serotonin ($pA_2$=9.13) and noradrenaline ($pA_2$=6.39). On the isolated rat uterus (see Jalon) it strongly inhibited serotonin ($2.47 \times 10^{-8}$M)-induced contractions ($IC_{50}$=$1.85 \times 10^{-9}$M).

It had no uterotonic activity (see Jalon).

On the isolated rabbit vena cava inferior the compound caused a minimal venous constriction ($1 \times 10^{-7}$M). On the isolated rabbit vena cava it inhibited the activity of noradrenaline on venous constrictions ($pA_2$=6.63).

An intravenous application of the compound in a dose of 450 µg/kg to pentobarbitalanesthetized normotensive rats caused a strong and sustained decrease in carotid artery pressure (by 20%) and in heart rate (by less than 20%) with respect to the initial level.

An intravenous application of the compound (450 µg/kg) to pithed rats (see Gillespie) caused a sustained mean increase in diastolic pressure by 20% with respect to the control level.

In urethane-anestetized normotensive rats the compound (450 µg/kg, i.v.) intensified the adrenaline (10 µg/kg, i.v.)-induced vasopressoric response.

After an i.p. application (5 mg/kg) the compound caused a strong dilatation of the pupil in mice (see Pulewka).

The binding studies showed that the compound possessed affinity to

[$^3$H] 8-OH-DPAT binding site (5-HT$_{1A}$ serotoninergic receptor); a further functional test did not indicate any activity;

[$^3$H] DTG binding site (sigma receptor); a further functional test indicated an antagonistic activity;

[$^3$H] pirenzepine binding site (M$_1$ muscarinic receptor); a further functional test indicated an antagonistic activity.

9,10,Didehydro-N-(2'-propinyl)-6-methylergoline-8β-carboxamide (compound of Example 1) and 2-bromo-9,10-didehydro-N-)2'-propinyl)-6-methylergoline-8β-carboxamide (compound of Example 2)

The binding studies showed that the compound of Example 1 exhibits a high affinity far the serotoninergic (5-HT$_{1A}$ and 5-HT$_2$) receptors and a lower affinity for the dopaminergic (D$_2$) receptors (Table 1). The compound of Example 2 shows a high affinity for the serotoninergic (5-HT$_2$) and dopaminergic (D$_2$) receptors and a somewhat lower affinity for the serotoninergic (5-HT$_{1A}$) receptors (Table 1).

TABLE 1

Binding affinities of the compounds of Examples 1 and 2 for the serotoninergic (5-HT$_{1A}$ and 5-HT$_2$) and dopaminergic (D$_2$) receptors

| Receptor | Radioligand | Ki (nM) Compound 1 | Ki (nM) Compound 2 |
| --- | --- | --- | --- |
| 5-HT$_{1A}$ | [$^3$H]8-OH-DPAT | 1.0 | 206.0 |
| 5-HT$_2$ | [$^3$H]Ketanserin | 64.0 | 90.0 |
| D$_2$ | [$^3$H]Raclopride | 151.0 | 44.0 |

The spontaneous tail-flicks in rats (without any outside stimulus) represent a specific pharmacological in vivo test since such a behavior in rats is known to be only caused by agonists having a highly marked intrinsic activity on the level of 5-HT$_{1A}$ receptors (the method was described by Millan, et al., Neurosci. Lett. 107,227–232, 1989). The head twitch model in mice represents an experimental model for determining the hallucinogenic action of a compound (the method was described by Handley and Singh, Br.J.Pharmacol., 86, 297–303, 1985). It is believed that the response is conveyed via the 5-HT$_2$ receptors.

Within the range of the tested doses (0.08 to 0.63 mg/kg s.c.), the compound of Example 1 provoked a dose- and time-dependent spontaneous tail-flick in rats. The effect is very similar to that caused by the selective 5-HT$_{1A}$ agonist 8-OH-DPAT. The i.p. application of the compound of Example 1 (0,078 to 5 mg/kg) caused a dose-dependent inhibition of the head twitch response in mice, which response had appeared after injection of 5-hydroxytryptophan/carbidopa, $ID_{50}$=0.74 mg/kg.

After i.p. application (2.5 to 20 mg/kg), the compound of Example 2 caused a dose-dependent inhibition of the head twitch response in mice, $ID_{50}$ =8.2 mg/kg. The compound of Example 2 when applied in a dose of 5.0 mg/kg s.c. did not cause a spontaneous tail-flick in rats. A preliminary treatment of rats with this compound (0.63 to 5.0 mg/kg s.c.) was found to strongly inhibit the spontaneous tail-flick in rats, which had been caused by the application of 8-OH-DPAT (2.5 mg/kg s.c.). The effect of the compound of Example 2 in this model was very similar to that of buspirone.

At present, the 5-HT$_{1A}$ and 5-HT$_2$ receptors are known to represent an important site of action in the central nervous system for the development of new anxiolytics and antidepressants.

TABLE 2

Binding affinities of the compounds of Examples 5 and 8 for the dopaminergic (D$_1$, D$_2$), serotoninergic (5-HT$_2$) and adrenergic ($\alpha_1$) receptors

| Receptor | Radioligand | Ki (nM) | |
|---|---|---|---|
| | | Compound 5 | Compound 8 |
| D$_1$ | [$^3$H]SCH23390 | 97.0 | 87.0 |
| D$_2$ | [$^3$H]Raclopride | 2.3 | 3.8 |
| 5-HT$_2$ | [$^3$H]Ketanserin | 18.0 | 10.0 |
| $\alpha_1$ | [$^3$H]Prazosin | 29.0 | 245.0 |

In two experimental models, i.e., apomorphine-induced locomotion and apomorphine-induced climbing tests in mice (the latter was described by Protais et al., Psychopharmacology, 50, 1–6, 1976), it was found that both compounds inhibit the characteristic behavior of animals, which was a result of apomorphine-induced activation of D2 receptors in CNS. The preliminary application (–45 min.) of the compound of Example 5 (0.25 to 2 mg/kg s.c.) and of the compound of Example 8 (0.0625 to 0.5 mg/kg s.c.), respectively, caused a dose-dependent inhibition of the apomorphine-induced (0.4 mg/kg s.c.) locomotion in rats (the respective ID$_{50}$ values amounted to 0.66 mg/kg and 0.089 mg/kg s.c.). The application of apomorphine in a dose of 1.5 mg/kg s.c. caused a characteristic climbing behavior in mice. The preliminary application (–30 min.) of the compound of Example 5 (2 to 8 mg/kg i.p.) and of the compound of Example 8 (0.125 to 1 mg/kg i.p.) caused a dose-dependent inhibition of climbing behavior (the respective ID$_{50}$ values amounted to 6.89 mg/kg and 0.44 mg/kg i.p.).

The s.c. application of the compounds of Example 5 (0.5 to 16 mg/kg) and of Example 8 (0.125 to 4 mg/kg), respectively, caused catalepsy in rats (the method was described by Morelli and Chiara, Europ. J. Pharmacol. 117, 179–185, 1985). The respective ED$_{50}$ values amounted to 1.4 mg/kg and 0.29 mg/kg s.c. The cataleptic action of both tested compounds was lesser than the action caused by the typical antipsychotic haloperidole (ED$_{50}$ =0.019 mg/kg s.c.).

The s.c. application of the compound of Example 5 (1 to 16 mg/kg) and of the compound of Example 8 (0.5 to 8 mg/kg) caused a dose-dependent inhibition of noradrenaline-induced lethality in rats, i.e., a response conveyed via $\alpha_1$ receptors. The respective ID$_{50}$ values were 5.11 mg/kg and 3.75 mg/kg s.c.

The $\alpha_1$-blocking action of both compounds was relatively weak if compared to their blocking action on the level of D$_2$ and 5-HT$_2$ receptors. The weak $\alpha_1$-blocking action of both compounds represents an advantage, since the blocking of these receptors is known to be involved in the development of hypotension and sedation.

The i.p. application of the compound of Example 8 (20 to 70 mg/kg) caused a dose-dependent inhibition of the oxotremorine-induced (1.5 mg/kg s.c.) tremor in mice, which is conveyed via acetylcholine receptors.

At using two models, i.e., inhibiting the spontaneous motor activity and increasing the pentobarbital-induced anesthesia in mice, it was found that the compounds of Examples 5 and 8 showed a several times lower depressant action on the level of CNS if compared with haloperidol. They showed a dose-dependent inhibition of the spontaneous motor activity in mice. The respective ID$_{50}$ values were 12.5 mg/kg and 8.4 mg/kg i.p. Both compounds also showed a dose-dependent prolongation of the pentobarbital-induced anesthesia in mice (the respective ED$_{50}$ values were 9.2 mg/kg and 17.1 mg/kg i.p.).

The i.v. application of the tested compounds to normotensive rats with pentobarbital-induced anesthesia caused a dose-dependent decrease of the mean arterial blood pressure respective ED$_{50}$ values were 0.42 mg/kg and 0.37 mg/kg).

What is claimed is:

1. A method of treating psychosis in a patient in a need of such treatment comprising administering to said patient, antipsychotically effective amount of an ergolinyl derivative of 2-propinylamine of the formula I

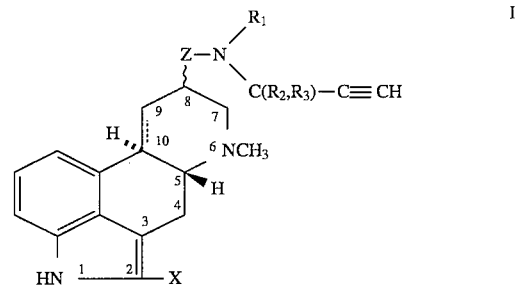

wherein,

R$_1$, R$_2$ and R$_3$ independently represent a hydrogen atom or a straight-chain or branched-chain C$_1$–C$_6$ alkyl group, X represents a hydrogen or a halogen atom, Z represents a carbonyl or methylene group and C$_9$ ⋯ C$_{10}$ represents a single or a double bond, diastereomeric forms, racemates and acid addition salts thereof.

2. The method of claim 1 wherein said derivative 5 is 2-Bromo-9,10-didehydro-N-methyl-N-(2'-propinyl)-6-methylergoline8β-carboxamide, or acid addition salt thereof.

3. The method of claim 1 wherein said derivative is 8β-Methyl-N-methyl-N-(2'propinyl)-6-methylergoline, or acid addition salt thereof.

* * * * *

UNITED STATES PATENT AND TRADEMARK OFFICE
CERTIFICATE OF CORRECTION

PATENT NO. : 5,480,885
DATED : January 2, 1996
INVENTOR(S) : Rucman et al

It is certified that error appears in the above-identified patent and that said Letters Patent is hereby corrected as shown below:

Title page, item [54] and col.1, lines 1-4, should read
---Ergoline Derivatives of 2-Propinylamine, a Process for the Manufacture Thereof and the Use Thereof for Medicaments---.

Title page, item [73] Assignee should read ---LEK, Tovarna Farmacevtskih in Kemicnih izdelkov, d.d., Ljubljana, Slovenia---.

Signed and Sealed this

Twenty-eighth Day of September, 1999

Attest:

Q. TODD DICKINSON

*Attesting Officer*    *Acting Commissioner of Patents and Trademarks*